(12) United States Patent
Warthoe

(10) Patent No.: US 6,271,004 B1
(45) Date of Patent: Aug. 7, 2001

(54) METHOD FOR IMPROVED REVERSE TRANSCRIPTION AT HIGH TEMPERATURES

(75) Inventor: Peter Warthoe, Copenhagen (DK)

(73) Assignee: Display Systems Biotech A/S, Copenhagen (DK)

( * ) Notice: Subject to any disclaimer, the term of this patent is extended or adjusted under 35 U.S.C. 154(b) by 0 days.

(21) Appl. No.: 09/603,185

(22) Filed: Jun. 26, 2000

(30) Foreign Application Priority Data

Jun. 25, 1999 (DK) .............................................. 1999 00897

(51) Int. Cl.[7] .............................. C12P 19/34; C12Q 1/68

(52) U.S. Cl. ................... 435/91.51; 435/91.1; 435/91.2; 435/91.5; 435/6

(58) Field of Search .............................. 435/91.51, 91.1, 435/188, 91.2, 6; 536/25.3, 24.33

(56) References Cited

U.S. PATENT DOCUMENTS

| | | | |
|---|---|---|---|
| 5,244,797 | 9/1993 | Kotewicz et al. | 435/194 |
| 5,405,776 | 4/1995 | Kotewicz et al. | 435/252.33 |
| 5,614,387 * | 3/1997 | Shen et al. | 435/91.2 |
| 5,668,005 | 9/1997 | Kotewicz et al. | 435/194 |
| 6,013,488 * | 1/2000 | Hayashizaki | 435/91.51 |

OTHER PUBLICATIONS

Science 250:954–958 (1990) "Molecular Chaperones; The Plant Connection." R. John Ellis.
Annu. Rev. Biochem. (1991) 60:321–47 "Molecular chaperones." Ellis,R.J., van der Vies, S.M.
Nature (1992) 355:33–45 "Protein folding in the cell." Gething, M.J., Sambrook, J.
Gene (1995) 164:153–6 "Aspartyl–tRNA synthetase of the hyperthermophilic archaeon Pyrococcus sp. KOD1 has a chimerical structure of eukaryotic and bacterial enzymes." Imanaka. T., Lee, S., Takagi, M., Fujiwara, S.
J. Biol. Chem. (1995) 270(48): 28818–23 "Conformational Cycle of the Archaeosome, a TCP1–like Chaperonin from *Sulfolobus shibatae*." Quaite–Randall E, Trent, J.D., Josephs R, Joachimiak A.
Appl. Enrivon. Microbiol. (1997) 63(2): 785–9. "In Vitro Stabilization and In Vivo Solubilization of Foreign Proteins by the beta Subunit of a Chaperonin from the Hyperthermophilic Archaeon Pyrococcus sp. Strain KOD1." Yan, Z., Fujiwara, S., Kohda, K., Takagi, M., Imanaka, T.
J. Mol. Biol. (1995) 253:712–25 "The 60 kDa Heat Shock Proteins in the Hyperthermophilic Archaeon *Sulfolobus shibatae*." Kagawa, H.K., Osipiuk, J., Maltsev, N., Overbeek, R., Quaite–Randall, E., Joachimiak, A., Trent, J.D.

(List continued on next page.)

Primary Examiner—Kenneth R. Horlick
Assistant Examiner—Alexander H. Spiegler
(74) Attorney, Agent, or Firm—Frommer Lawrence & Haug LLP; Thomas J. Kowalski

(57) ABSTRACT

The invention relates to a method for enzyme stabilization. A method for improved reverse transcription at high temperatures is provided, wherein a thermostable heat shock protein (HSPs) stabilizes a reverse transcriptase, as well as reduces the RNase H activity of said reverse transcriptase. The present invention thus relates to a stabilizing agent, that prevents thermal denaturing and enhances thermostability of a reverse transcriptase. The invention further relates to a method of producing a polypeptide complex consisting of a Chaperonin and a Moloney murine leukemia virus (MMVL) reverse transcriptase, characterized by having enhanced thermostability as well as reduced RNase H activity, compared to a (MMVL) reverse transcriptase alone. The invention further relates to a kit for the preparation of cDNA from mRNA, comprising either both stabilizing agent and reverse transcriptase or the polypeptide complex of the invention.

39 Claims, 10 Drawing Sheets

OTHER PUBLICATIONS

Proc. Natl. Acad. Sci., U S A. (1988) 85(6): 1777–81. "Domain structure of the Moloney murine leukemia virus reverse transcriptase: Mutational analysis and separate expression of the DNA polymerase and RNase H activities." Tanese, N.,. Goff, S.P.

J. Virol. (1975) 15(4): 785–97 "Purification and Characterization of the DNA Polymerase and RNase H Activities in Moloney Murine Sarcoma–Leukemia Virus." Gerard, G.F., Grandgenett, D.P.

Proteins (1998) 33:135–43 "Folding the Ribonuclease H Domain of Moloney Murine Leukemia Virus Reverse Transcriptase Requires Metal Binding or a Short N–Terminal Extension." Goedken, E.R., Marqusee, S.

Science (1990) 249:1398–405 "Structure of Ribonuclease H Phased at 2 A Resolution by MAD Analysis of the Selenomethionyl Protein." Yang, W., Hendrickson, W.A., Crouch, R.J., Satow, Y.

Nature (1990) 347:306–9 "Three dimensional structure of ribonuclease H from *E. coli*." Katayanagi, K., Miyagawa, M., Matsushima, M., Ishikawa, M., Kanaya S, Ikehara, M, Matsuzaki, T, Morikawa, K.

J. Mol. Biol. (1993) 230:529–42 "Crystal Structure of Ribonuclease H from *Thermus thermophilus*, HB8 Refined at 2.8 A Resolution." Shikawa, K., Okumura, M., Katayanagi, K., Kimura, S., Kanaya, S., Nakamura, H., Morikawa, K.

Science (1991) 252:88–95 "Crystal Structure of the Ribonuclease H. Domain of HIV–1 Reverse Transcriptase." Davies, J.F. 2d, Hostomska,Z., Hostomsky, Z., Jordan, S.R., Matthews, D.A.

Biochemistry (1983) 22(10): 2365–72 "Reverse Transcriptase and Its Associated Ribonuclease H: Interplay of Two Enzyme Activities Controls the Yield of Single–Stranded Complementary Deoxyribonucleic Acid." Berger, S.L., Wallace, D.M., Puskas, R.S., Eschenfeldt, W.H.

Sambrook et al. "Synthesis of cDNA." Molecular Cloning: A Labortory Manual (1982) 213–216.

Proc. Natl. Acad. Sci. U S A (1981) 78(12): 7609–13 "DNA methylation and gene expression: Endogenous retroviral genome becomes infectious after molecular cloning." Harbers, K., Schnieke, A., Stuhlmann, H., Jahner, D., Jaenisch, R.

J. Virol. Methods (1980) 1:157–65 "Purification of reverse transcriptase from avian retroviruses using affinity chromatogaphy on heparin–sepharose." Golomb, M., Vora, A.C., Grandgenett, D.P.

Biochemistry Jun. 13, 1978;17(12):2438–42 Discrimination of DNA polymerase and RNase H activities in reverse transcriptase of avian myeloblastosis virus. Gorecki, .and Panet, A.

J Virol Dec. 1974;14(6):1494 Mechanistic independence of avian myeloblastosis virus DNA polymerase and ribonuclease H. Brewer, L.C., Wells, R,D., Brewer, L.C., & Wells, R. D.

Biochem Biophys Res. Commun Jul. 16, 1981;101(1):183–8 The artifactual nature of fluoride inhibition of reverse transcriptase and associated ribonuclease H. Srivastava, S.K., Gillerman, E., Modak, M.J.

Differential Effects of Captan on DNA Polymerase and Ribonuclease H activities of Avian Myeloblastosis Virus Reverse Transcriptase. Freeman–Witti, M. J., Vinocour, M. and Lewis R. A. ( 1986) Biochemistry, 25, 3050–3055.

The role of Moloney Murine Leukemia Virus Rnase H activity in the formation of Plus– Strand Primers Rattray A.J. and Champoux J.J. ( 1987) J. Virology, Sep., 2843–2851.

Computer Analysis of retroviral pol genes: Assignment of enzymatic functions to specific sequences and homologies with non–viral enzymes Proc. Natl. Acad. Sci. U.S.A (1986) vol. 83, 7648–7652 Johnson, M.S., McClure,M.A., Feng, D.F., Gray, J. and Doolittle, R. F.

* cited by examiner

FIGURE. 2 – DNA Sequence STR 1

```
  1 TTGACCCTAAATATAGAAGATGAGCATGGGCTACATGAGACCTCAAAAAGAGACCCTGTCTGATTTCCTCAGGCCTGTCTGATTTCCTCAGGCCGAAACCGGGGGCATG  120
  1  M  T  L  N  I  E  D  E  H  R  L  H  E  T  S  K  E  P  D  V  S  L  G  S  T  W  L  S  D  F  P  Q  A  W  A  E  T  G  G  M   40

121 GGACTGGCAGTTCGCCAAGCTCCTCGATCATACCTCTGAAAAGCTAAAACAATACCCATGTCATAAAACAATACCCTACCCCGTGTCATAAAACAATACCCTACCCCGTGTCATAAAACAATACAG  240
 41  G  L  A  V  R  Q  A  P  L  I  I  P  L  K  A  T  S  T  P  V  S  I  K  Q  Y  P  M  B  Q  E  A  R  L  G  I  K  P  H  I  Q   80

241 AGACTGTTGGACCAGGGAATACTGGTACCCCTGGAACACGCTGGAACACCAGGACTAATGATTATAGGCCTGTCCAGATCTGAGAGAAGTCAAC  360
 81  R  L  L  D  Q  G  I  L  V  P  C  Q  S  P  W  N  T  P  L  L  P  V  K  K  P  G  T  N  D  Y  R  P  V  Q  D  L  R  E  V  N  120

361 AAGCGGGTGGAAGACATCCACCCTACCAGTGTGCCTCAACCCTCTGAGGGGGCTGGGACTAGTTAAAGGATGCCTTTTCTGCCTGAGA  480
121  K  R  V  E  D  I  H  P  T  V  P  N  P  Y  N  L  L  S  G  L  P  P  E  H  Q  W  Y  T  V  L  D  L  K  D  A  F  F  C  L  R  160

481 CTCCACCCCACCAGTCAGCCTCTCTCGCCTTTGAGTGGAGAGATCCAGAGATGGGAATCCAGAGACCAATTGACCTGGACCAGAGTCCCACAGGGTTTCAAAAACAGTCCCACCCTGTT  600
161  L  H  P  T  S  Q  P  L  P  A  P  E  W  R  D  P  P  M  G  I  S  G  Q  L  T  W  T  R  L  P  Q  G  F  K  N  S  P  T  L  F  200

601 GATGAGGCACTGCACAGAGACTTAGCAGACTTCCGGATCCAGCATCCTGCTACAGCTGATGATTACTGTGGCCACTTACTGCTAGCTACAAGGT  720
201  D  E  A  L  H  R  D  L  A  D  F  R  I  Q  H  P  D  L  I  L  L  Q  Y  V  D  D  L  L  L  A  A  T  S  E  L  D  C  Q  Q  G  240

721 ACTCGGGCCCGTGTTACAAACCCTAACGGGAATCTGATGGGCAGCCTACTCCGAAGACCCCTCGACACAACTAAGGGACGGTTCCTAGGGACGGGTTCGAGAGATGG  840
241  T  R  A  L  L  Q  T  L  G  Y  R  A  S  A  K  K  A  Q  I  C  Q  K  Q  V  K  Y  L  G  Y  L  L  K  E  G  Q  R  W  280

841 CTGACTGAGGCCAGAAAAGAGACTGTGATGGGCAGGCAGCCTACCAAAACGGGGACTCTCTTGTACCCCCTGTAATTGGGGCAGCAGTCAGCAGCAA  960
281  L  T  E  A  R  K  E  T  V  M  G  Q  P  T  P  K  T  P  R  Q  L  R  E  F  L  G  T  A  G  F  C  R  L  W  I  P  G  F  A  E  320

961 ATGGCAGCCCCCCTGTACTAGCCCCTTTGACTCTCTTGTCGACGAGAGCAGGAGCAGTGTCCTAACGCAAAACTGGACCTTGGCGTTGGCGTTGGCGTGGCCTACTCTGTCCAAAAGCTA  1080
321  M  A  A  P  L  Y  P  L  T  K  T  G  T  L  F  N  W  G  P  D  Q  Q  K  A  Y  Q  E  I  K  Q  A  L  L  T  A  P  A  L  G  L  360

1081 CCAGATTTGACTAAGCCCTTTGACTAAGCCCCTTTGACTAAGCCCCTTTGACTAAGCCCCTTTGACTAAGCCCCTTTGAC  1200
361  P  D  L  T  K  P  F  F  E  L  F  V  D  E  K  Q  G  Y  A  K  G  V  L  T  Q  K  L  G  P  W  R  R  P  V  A  Y  L  S  K  L  400

1201 GACCCAGTAGCAGCTGGATGGCCCTAGCGGATGGTAGCCCTGCCTACGATCATTCTGGCCCCCATGCA  1320
401  D  P  V  A  A  G  W  P  P  C  L  R  M  V  A  A  I  A  V  L  T  K  D  A  G  K  L  T  M  G  Q  P  L  V  I  L  A  P  H  A  440

1321 GTAGAGGCACTAGTCAAACAACCCCCGACCGCTGGCTTTCAACGCCCGGATGACTACTATCAGGCCCTGCTTTTGGACCTGGACACGGACCGGGGTCAGTTCGGACCGGGGTCAGTTAAC  1440
441  V  E  A  L  V  K  Q  P  P  D  R  W  L  S  N  A  R  M  T  H  W  Q  A  L  L  D  T  D  R  V  Q  F  G  P  V  V  A  L  N  480

1441 CCGGCTACCGCTCCTCCACTGCCTGAGGAAGGGCTGCAACAACAAACTGCCCTTGATATCCTGGCCGAAGGACCCGACCTAACGGACCAGCAGCCGCTCTAA
481  P  A  T  L  L  P  L  P  E  E  G  L  Q  H  N  C  L  D  I  L  A  E  A  H  G  T  R  P  D  L  T  D  Q  P  L  *
```

FIGURE. 5 — DNA Sequence STR 2

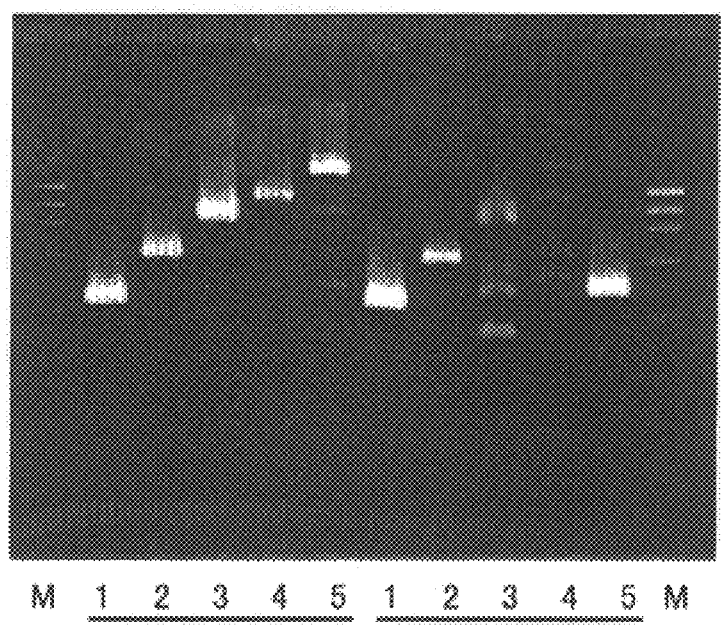
M ; Marker ΦX174/Hae III
1 ; Target size 336 bp
2 ; Target size 603 bp
3 ; Target size 953 bp
4 ; Target size 1223 bp
5 ; Target size 1758 bp
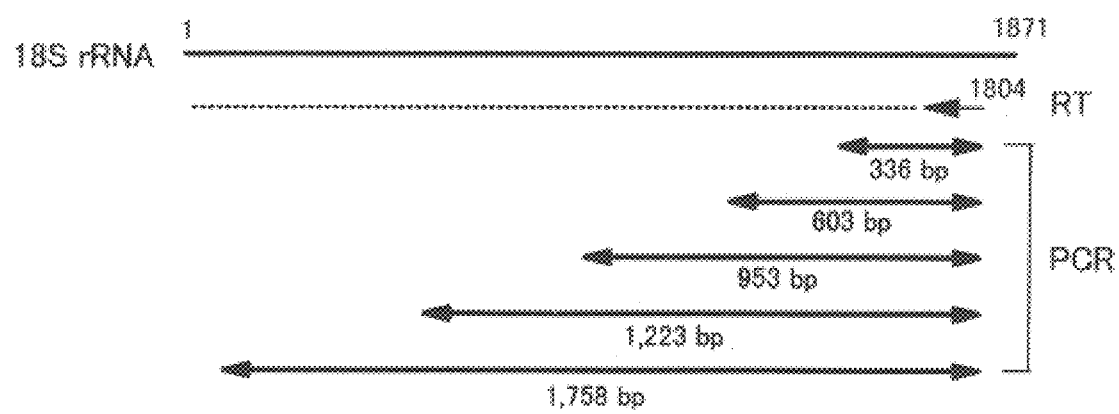
FIGURE. 9

SEQUENCE LISTING

<160> NUMBER OF SEQ ID NOS: 8

<210> SEQ ID NO 1
<211> LENGTH: 1680
<212> TYPE: DNA
<213> ORGANISM: Pyrococcus sp.
<220> FEATURE:
<221> NAME/KEY: CDS
<222> LOCATION: (39)..(1637)

<400> SEQUENCE: 1

```
ccaccctcaa aaacaaaaaa gggtgggggt gaggggag atg gcc cag ctc gca ggc      56
                                          Met Ala Gln Leu Ala Gly
                                          1               5 cag cca gtt gtt att ctg ccc gag gga acc cag agg tat gtt gga agg     104
Gln Pro Val Val Ile Leu Pro Glu Gly Thr Gln Arg Tyr Val Gly Arg
            10                  15                  20 gac gcc cag agg ctc aac att ctt gct gcc agg att ata gcc gag acg     152
Asp Ala Gln Arg Leu Asn Ile Leu Ala Ala Arg Ile Ile Ala Glu Thr
        25                  30                  35 gtt aga acc acc ctc ggt cca aag gga atg gac aag atg ctc gtt gac     200
Val Arg Thr Thr Leu Gly Pro Lys Gly Met Asp Lys Met Leu Val Asp
    40                  45                  50 agc ctc ggc gac atc gtc atc acc aac gac ggt gca acc att ctc gac     248
```

-continued

```
Ser Leu Gly Asp Ile Val Ile Thr Asn Asp Gly Ala Thr Ile Leu Asp
55                  60                  65                  70 gag atg gac atc cag cac cct gct gct aag atg atg gtt gag gtt gct      296
Glu Met Asp Ile Gln His Pro Ala Ala Lys Met Met Val Glu Val Ala
                    75                  80                  85 aag act cag gac aag gag gcc ggt gac gga acc acc act gcc gtt gtc      344
Lys Thr Gln Asp Lys Glu Ala Gly Asp Gly Thr Thr Thr Ala Val Val
                90                  95                  100 atc gcc ggt gag ctt ctg agg aag gct gag gag ctt ctc gac cag aac      392
Ile Ala Gly Glu Leu Leu Arg Lys Ala Glu Glu Leu Leu Asp Gln Asn
            105                 110                 115 att cac ccg agc ata atc atc aag ggt tac gcc ctc gcg gca gag aaa      440
Ile His Pro Ser Ile Ile Ile Lys Gly Tyr Ala Leu Ala Ala Glu Lys
        120                 125                 130 gcc cag gaa ata ctc gac gag ata gcc aag gac gtt gac gtc gag gac      488
Ala Gln Glu Ile Leu Asp Glu Ile Ala Lys Asp Val Asp Val Glu Asp
135                 140                 145                 150 agg gag att ctc aag aag gcc gcg gtc acc tcc atc acc gga aag gct      536
Arg Glu Ile Leu Lys Lys Ala Ala Val Thr Ser Ile Thr Gly Lys Ala
                    155                 160                 165 gcc gag gag gag agg gag tac ctc gct gag ata gca gtt gag gcc gtc      584
Ala Glu Glu Glu Arg Glu Tyr Leu Ala Glu Ile Ala Val Glu Ala Val
                170                 175                 180 aag cag gtt gcc gag aag gtt ggc gag acc tac aag gtc gac ctc gac      632
Lys Gln Val Ala Glu Lys Val Gly Glu Thr Tyr Lys Val Asp Leu Asp
            185                 190                 195 aac atc aag ttc gag aag aag gaa ggt gga agc gtc aag gac acc cag      680
Asn Ile Lys Phe Glu Lys Lys Glu Gly Gly Ser Val Lys Asp Thr Gln
        200                 205                 210 ctc ata aag ggt gtc gtc atc gac aag gag gtc gtc cac cca ggc atg      728
Leu Ile Lys Gly Val Val Ile Asp Lys Glu Val Val His Pro Gly Met
215                 220                 225                 230 ccg aag agg gtc gag ggt gct aag atc gcc ctc atc aac gag gcc ctc      776
Pro Lys Arg Val Glu Gly Ala Lys Ile Ala Leu Ile Asn Glu Ala Leu
                    235                 240                 245 gag gtc aag gag acc gag acc gac gcc gag atc agg atc acc agc ccg      824
Glu Val Lys Glu Thr Glu Thr Asp Ala Glu Ile Arg Ile Thr Ser Pro
                250                 255                 260 gag cag ctc cag gcc ttc ctt gag cag gag gag aag atg ctc agg gag      872
Glu Gln Leu Gln Ala Phe Leu Glu Gln Glu Glu Lys Met Leu Arg Glu
            265                 270                 275 atg gtc gac aag atc aag gag gtc ggc gcg aat gtc gtc ttc gtc cag      920
Met Val Asp Lys Ile Lys Glu Val Gly Ala Asn Val Val Phe Val Gln
        280                 285                 290 aag ggc att gac gac ctc gcc cag cac tac ctt gcc aag tac ggc ata      968
Lys Gly Ile Asp Asp Leu Ala Gln His Tyr Leu Ala Lys Tyr Gly Ile
295                 300                 305                 310 atg gcc gtt aga agg gtc aag aag agc gac atg gag aag ctc gcc aag      1016
Met Ala Val Arg Arg Val Lys Lys Ser Asp Met Glu Lys Leu Ala Lys
                    315                 320                 325 gcc acc ggc gcc aag atc gtc acc aac gtc cgc gac ctc act ccg gag      1064
Ala Thr Gly Ala Lys Ile Val Thr Asn Val Arg Asp Leu Thr Pro Glu
                330                 335                 340 gac ctc ggt gag gcc gag ctc gtc gag cag agg aag gtc gcc ggc gag      1112
Asp Leu Gly Glu Ala Glu Leu Val Glu Gln Arg Lys Val Ala Gly Glu
            345                 350                 355 aac atg atc ttc gtc gag ggc tgc aag aac ccg aag gcc gtc aca ata      1160
Asn Met Ile Phe Val Glu Gly Cys Lys Asn Pro Lys Ala Val Thr Ile
        360                 365                 370
```

-continued

| | | | | | | | | | | | | | | | |
|---|---|---|---|---|---|---|---|---|---|---|---|---|---|---|---|
| ctc | atc | agg | ggc | ggc | acc | gag | cac | gtc | gtt | gat | gag | gtc | gag | agg | gcc | 1208 |
| Leu | Ile | Arg | Gly | Gly | Thr | Glu | His | Val | Val | Asp | Glu | Val | Glu | Arg | Ala |
| 375 | | | | 380 | | | | | 385 | | | | | 390 | |

| ctt | gag | gac | gcc | gtc | aag | gtc | gtc | aag | gac | atc | gtc | gag | gac | ggc | aag | 1256 |
| Leu | Glu | Asp | Ala | Val | Lys | Val | Val | Lys | Asp | Ile | Val | Glu | Asp | Gly | Lys |
| | | | | 395 | | | | | 400 | | | | | 405 | |

| atc | gtc | gcc | gcc | ggt | ggt | gct | ccg | gag | atc | gag | ctc | gcc | atc | agg | ctc | 1304 |
| Ile | Val | Ala | Ala | Gly | Gly | Ala | Pro | Glu | Ile | Glu | Leu | Ala | Ile | Arg | Leu |
| | | | 410 | | | | | 415 | | | | | 420 | | |

| gac | gag | tac | gcg | aag | gag | gtc | ggc | ggc | aag | gag | cag | ctc | gcc | atc | gag | 1352 |
| Asp | Glu | Tyr | Ala | Lys | Glu | Val | Gly | Gly | Lys | Glu | Gln | Leu | Ala | Ile | Glu |
| | | 425 | | | | | 430 | | | | | 435 | | | |

| gcc | ttt | gcc | gag | gcc | ctc | aag | gtc | atc | ccg | agg | acc | ctc | gcc | gag | aac | 1400 |
| Ala | Phe | Ala | Glu | Ala | Leu | Lys | Val | Ile | Pro | Arg | Thr | Leu | Ala | Glu | Asn |
| | 440 | | | | | 445 | | | | | 450 | | | | |

| gcc | ggt | ctc | gac | ccg | atc | gag | acc | ctc | gtt | aag | gtc | atc | gcc | gcc | cac | 1448 |
| Ala | Gly | Leu | Asp | Pro | Ile | Glu | Thr | Leu | Val | Lys | Val | Ile | Ala | Ala | His |
| 455 | | | | 460 | | | | | 465 | | | | | 470 | |

| aag | gag | aag | gga | ccg | acc | atc | ggt | gtt | gac | gtc | ttc | gag | ggc | gag | ccg | 1496 |
| Lys | Glu | Lys | Gly | Pro | Thr | Ile | Gly | Val | Asp | Val | Phe | Glu | Gly | Glu | Pro |
| | | | | 475 | | | | | 480 | | | | | 485 | |

| gcc | gac | atg | ctc | gag | cgc | ggc | gtt | atc | gcc | ccg | gtc | agg | gtt | ccg | aag | 1544 |
| Ala | Asp | Met | Leu | Glu | Arg | Gly | Val | Ile | Ala | Pro | Val | Arg | Val | Pro | Lys |
| | | | 490 | | | | | 495 | | | | | 500 | | |

| cag | gcc | atc | aag | agc | gcc | agc | gag | gct | gcc | ata | atg | atc | ctc | agg | atc | 1592 |
| Gln | Ala | Ile | Lys | Ser | Ala | Ser | Glu | Ala | Ala | Ile | Met | Ile | Leu | Arg | Ile |
| | | 505 | | | | | 510 | | | | | 515 | | | |

| gac | gac | gtc | atc | gcc | gcc | agc | aag | ctc | gag | aag | gac | aag | gag | ggc | | 1637 |
| Asp | Asp | Val | Ile | Ala | Ala | Ser | Lys | Leu | Glu | Lys | Asp | Lys | Glu | Gly |
| | | 520 | | | | | 525 | | | | | 530 | | | | tgaaagggcg gtagcgagga tttcggaagc gaccttgact gaa    1680

<210> SEQ ID NO 2
<211> LENGTH: 533
<212> TYPE: PRT
<213> ORGANISM: Pyrococcus sp.

<400> SEQUENCE: 2

Met Ala Gln Leu Ala Gly Gln Pro Val Val Ile Leu Pro Glu Gly Thr
1               5                   10                  15

Gln Arg Tyr Val Gly Arg Asp Ala Gln Arg Leu Asn Ile Leu Ala Ala
                20                  25                  30

Arg Ile Ile Ala Glu Thr Val Arg Thr Thr Leu Gly Pro Lys Gly Met
            35                  40                  45

Asp Lys Met Leu Val Asp Ser Leu Gly Asp Ile Val Ile Thr Asn Asp
        50                  55                  60

Gly Ala Thr Ile Leu Asp Glu Met Asp Ile Gln His Pro Ala Ala Lys
65                  70                  75                  80

Met Met Val Glu Val Ala Lys Thr Gln Asp Lys Glu Ala Gly Asp Gly
                85                  90                  95

Thr Thr Thr Ala Val Val Ile Ala Gly Glu Leu Leu Arg Lys Ala Glu
                100                 105                 110

Glu Leu Leu Asp Gln Asn Ile His Pro Ser Ile Ile Lys Gly Tyr
            115                 120                 125

Ala Leu Ala Ala Glu Lys Ala Gln Glu Ile Leu Asp Glu Ile Ala Lys
        130                 135                 140

Asp Val Asp Val Glu Asp Arg Glu Ile Leu Lys Lys Ala Ala Val Thr
145                 150                 155                 160

```
Ser Ile Thr Gly Lys Ala Ala Glu Glu Arg Glu Tyr Leu Ala Glu
            165                 170                 175

Ile Ala Val Glu Ala Val Lys Gln Val Ala Glu Lys Val Gly Glu Thr
            180                 185                 190

Tyr Lys Val Asp Leu Asp Asn Ile Lys Phe Glu Lys Lys Glu Gly Gly
            195                 200                 205

Ser Val Lys Asp Thr Gln Leu Ile Lys Gly Val Val Ile Asp Lys Glu
            210                 215                 220

Val Val His Pro Gly Met Pro Lys Arg Val Glu Gly Ala Lys Ile Ala
225                 230                 235                 240

Leu Ile Asn Glu Ala Leu Glu Val Lys Glu Thr Glu Thr Asp Ala Glu
            245                 250                 255

Ile Arg Ile Thr Ser Pro Glu Gln Leu Gln Ala Phe Leu Glu Gln Glu
            260                 265                 270

Glu Lys Met Leu Arg Glu Met Val Asp Lys Ile Lys Glu Val Gly Ala
            275                 280                 285

Asn Val Val Phe Val Gln Lys Gly Ile Asp Asp Leu Ala Gln His Tyr
            290                 295                 300

Leu Ala Lys Tyr Gly Ile Met Ala Val Arg Arg Val Lys Lys Ser Asp
305                 310                 315                 320

Met Glu Lys Leu Ala Lys Ala Thr Gly Ala Lys Ile Val Thr Asn Val
            325                 330                 335

Arg Asp Leu Thr Pro Glu Asp Leu Gly Glu Ala Glu Leu Val Glu Gln
            340                 345                 350

Arg Lys Val Ala Gly Glu Asn Met Ile Phe Val Glu Gly Cys Lys Asn
            355                 360                 365

Pro Lys Ala Val Thr Ile Leu Ile Arg Gly Gly Thr Glu His Val Val
            370                 375                 380

Asp Glu Val Glu Arg Ala Leu Glu Asp Ala Val Lys Val Val Lys Asp
385                 390                 395                 400

Ile Val Glu Asp Gly Lys Ile Val Ala Ala Gly Gly Ala Pro Glu Ile
            405                 410                 415

Glu Leu Ala Ile Arg Leu Asp Glu Tyr Ala Lys Glu Val Gly Gly Lys
            420                 425                 430

Glu Gln Leu Ala Ile Glu Ala Phe Ala Glu Ala Leu Lys Val Ile Pro
            435                 440                 445

Arg Thr Leu Ala Glu Asn Ala Gly Leu Asp Pro Ile Glu Thr Leu Val
            450                 455                 460

Lys Val Ile Ala Ala His Lys Glu Lys Gly Pro Thr Ile Gly Val Asp
465                 470                 475                 480

Val Phe Glu Gly Glu Pro Ala Asp Met Leu Glu Arg Gly Val Ile Ala
            485                 490                 495

Pro Val Arg Val Pro Lys Gln Ala Ile Lys Ser Ala Ser Glu Ala Ala
            500                 505                 510

Ile Met Ile Leu Arg Ile Asp Asp Val Ile Ala Ala Ser Lys Leu Glu
            515                 520                 525

Lys Asp Lys Glu Gly
    530

<210> SEQ ID NO 3
<211> LENGTH: 26
<212> TYPE: PRT
<213> ORGANISM: Moloney murine leukemia virus
```

```
<400> SEQUENCE: 3

Pro Glu Glu Gly Leu Gln His His Cys Leu Asp Ile Leu Ala Glu Ala
1               5                   10                  15

His Gly Thr Arg Pro Asp Leu Thr Asp Gln
            20                  25

<210> SEQ ID NO 4
<211> LENGTH: 18
<212> TYPE: PRT
<213> ORGANISM: Moloney murine leukemia virus

<400> SEQUENCE: 4

Asp Ile Leu Ala Glu Ala His Gly Thr Arg Pro Asp Leu Thr Asp Gln
1               5                   10                  15

Pro Leu

<210> SEQ ID NO 5
<211> LENGTH: 1140
<212> TYPE: DNA
<213> ORGANISM: Moloney murine leukamia virus
<220> FEATURE:
<221> NAME/KEY: CDS
<222> LOCATION: (1)..(1137)

<400> SEQUENCE: 5 atg acc cta aat ata gaa gat gag cat cgg cta cat gag acc tca aaa      48
Met Thr Leu Asn Ile Glu Asp Glu His Arg Leu His Glu Thr Ser Lys
1               5                   10                  15 gag cca gat gtt tct cta ggg tcc aca tgg ctg tct gat ttt cct cag      96
Glu Pro Asp Val Ser Leu Gly Ser Thr Trp Leu Ser Asp Phe Pro Gln
            20                  25                  30 gcc tgg gcg gaa acc ggg ggc atg gga ctg gca gtt cgc caa gct cct     144
Ala Trp Ala Glu Thr Gly Gly Met Gly Leu Ala Val Arg Gln Ala Pro
        35                  40                  45 ctg atc ata cct ctg aaa gca acc tct acc ccc gtg tcc ata aaa caa     192
Leu Ile Ile Pro Leu Lys Ala Thr Ser Thr Pro Val Ser Ile Lys Gln
    50                  55                  60 tac ccc atg tca caa gaa gcc aga ctg ggg atc aag ccc cac ata cag     240
Tyr Pro Met Ser Gln Glu Ala Arg Leu Gly Ile Lys Pro His Ile Gln
65                  70                  75                  80 aga ctg ttg gac cag gga ata ctg gta ccc tgc cag tcc ccc tgg aac     288
Arg Leu Leu Asp Gln Gly Ile Leu Val Pro Cys Gln Ser Pro Trp Asn
                85                  90                  95 acg ccc ctg cta ccc gtt aag aaa cca ggg act aat gat tat agg cct     336
Thr Pro Leu Leu Pro Val Lys Lys Pro Gly Thr Asn Asp Tyr Arg Pro
            100                 105                 110 gtc cag gat ctg aga gaa gtc aac aag cgg gtg gaa gac atc cac ccc     384
Val Gln Asp Leu Arg Glu Val Asn Lys Arg Val Glu Asp Ile His Pro
        115                 120                 125 acc gtg ccc aac cct tac aac ctc ttg agc ggg ctc cca ccg tcc cac     432
Thr Val Pro Asn Pro Tyr Asn Leu Leu Ser Gly Leu Pro Pro Ser His
    130                 135                 140 cag tgg tac act gtg ctt gat tta aag gat gcc ttt ttc tgc ctg aga     480
Gln Trp Tyr Thr Val Leu Asp Leu Lys Asp Ala Phe Phe Cys Leu Arg
145                 150                 155                 160 ctc cac ccc acc agt cag cct ctc ttc gcc ttt gag tgg aga gat cca     528
Leu His Pro Thr Ser Gln Pro Leu Phe Ala Phe Glu Trp Arg Asp Pro
                165                 170                 175 gag atg gga atc tca gga caa ttg acc tgg acc aga ctc cca cag ggt     576
Glu Met Gly Ile Ser Gly Gln Leu Thr Trp Thr Arg Leu Pro Gln Gly
            180                 185                 190
```

```
ttc aaa aac agt ccc acc ctg ttt gat gag gca ctg cac aga gac cta      624
Phe Lys Asn Ser Pro Thr Leu Phe Asp Glu Ala Leu His Arg Asp Leu
        195                 200                 205 gca gac ttc cgg atc cag cac cca gac ttg atc ctg cta cag tac gtg      672
Ala Asp Phe Arg Ile Gln His Pro Asp Leu Ile Leu Leu Gln Tyr Val
    210                 215                 220 gat gac tta ctg ctg gcc gcc act tct gag cta gac tgc caa caa ggt      720
Asp Asp Leu Leu Leu Ala Ala Thr Ser Glu Leu Asp Cys Gln Gln Gly
225                 230                 235                 240 act cgg gcc ctg tta caa acc cta ggg aac ctc ggg tat cgg gcc tcg      768
Thr Arg Ala Leu Leu Gln Thr Leu Gly Asn Leu Gly Tyr Arg Ala Ser
            245                 250                 255 gcc aag aaa gcc caa att tgc cag aaa cag gtc aag tat ctg ggg tat      816
Ala Lys Lys Ala Gln Ile Cys Gln Lys Gln Val Lys Tyr Leu Gly Tyr
        260                 265                 270 ctt cta aaa gag ggt cag aga tgg ctg act gag gcc aga aaa gag act      864
Leu Leu Lys Glu Gly Gln Arg Trp Leu Thr Glu Ala Arg Lys Glu Thr
    275                 280                 285 gtg atg ggg cag cct act ccg aag acc cct cga caa cta agg gag ttc      912
Val Met Gly Gln Pro Thr Pro Lys Thr Pro Arg Gln Leu Arg Glu Phe
290                 295                 300 cta ggg acg gca ggc ttc tgt cgc ctc tgg atc cct ggg ttt gca gaa      960
Leu Gly Thr Ala Gly Phe Cys Arg Leu Trp Ile Pro Gly Phe Ala Glu
305                 310                 315                 320 atg gca gcc ccc ttg tac cct ctc acc aaa acg ggg act ctg ttt aat     1008
Met Ala Ala Pro Leu Tyr Pro Leu Thr Lys Thr Gly Thr Leu Phe Asn
            325                 330                 335 tgg ggc cca gac caa caa aag gcc tat caa gaa atc aag caa gct ctt     1056
Trp Gly Pro Asp Gln Gln Lys Ala Tyr Gln Glu Ile Lys Gln Ala Leu
        340                 345                 350 cta act gcc cca gcc ctg ggg ttg cca gat ttg act aag ccc ttt gaa     1104
Leu Thr Ala Pro Ala Leu Gly Leu Pro Asp Leu Thr Lys Pro Phe Glu
    355                 360                 365 ctc ttt gtc gac gag aag cag ggc tac gcc aaa ggt                     1140
Leu Phe Val Asp Glu Lys Gln Gly Tyr Ala Lys
    370                 375

<210> SEQ ID NO 6
<211> LENGTH: 379
<212> TYPE: PRT
<213> ORGANISM: Moloney murine leukamia virus

<400> SEQUENCE: 6

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
            85                  90                  95

Thr Pro Leu Leu Pro Val Lys Lys Pro Gly Thr Asn Asp Tyr Arg Pro
        100                 105                 110

Val Gln Asp Leu Arg Glu Val Asn Lys Arg Val Glu Asp Ile His Pro
```

-continued

```
                115                 120                 125
    Thr Val Pro Asn Pro Tyr Asn Leu Leu Ser Gly Leu Pro Pro Ser His
            130                 135                 140

Gln Trp Tyr Thr Val Leu Asp Leu Lys Asp Ala Phe Phe Cys Leu Arg
    145                 150                 155                 160

Leu His Pro Thr Ser Gln Pro Leu Phe Ala Phe Glu Trp Arg Asp Pro
                    165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
    225                 230                 235                 240

Thr Arg Ala Leu Leu Gln Thr Leu Gly Asn Leu Gly Tyr Arg Ala Ser
                    245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
        290                 295                 300

Leu Gly Thr Ala Gly Phe Cys Arg Leu Trp Ile Pro Gly Phe Ala Glu
    305                 310                 315                 320

Met Ala Ala Pro Leu Tyr Pro Leu Thr Lys Thr Gly Thr Leu Phe Asn
                    325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys
        370                 375

<210> SEQ ID NO 7
<211> LENGTH: 32
<212> TYPE: DNA
<213> ORGANISM: Artificial
<220> FEATURE:
<223> OTHER INFORMATION: primer

<400> SEQUENCE: 7
ggcaggggcc atggcccagc tcgcaggcca gc                                32

<210> SEQ ID NO 8
<211> LENGTH: 32
<212> TYPE: DNA
<213> ORGANISM: Artificial
<220> FEATURE:
<223> OTHER INFORMATION: primer

<400> SEQUENCE: 8
gcgcaaaagg gatccaaggt catcagtcaa gg                                32
```

METHOD FOR IMPROVED REVERSE TRANSCRIPTION AT HIGH TEMPERATURES

RELATED APPLICATIONS

This application claims priority from Danish application 1999 00897, filed Jun. 25, 1999. Reference is also made to U.S. Ser. No. 09/068,860, filed May 19, 1998, now allowed. Each of the foregoing applications, patents and publications and all documents cited or referenced therein ("application cited documents") and all documents cited or referenced in this specification ("herein cited documents") and all documents referenced or cited in herein cited documents and in application cited documents, including during the prosecution of any of the application cited documents, are hereby incorporated herein by reference.

FIELD OF THE INVENTION

The invention is in the field of recombinant genetics.

BACKGROUND OF THE INVENTION

Reverse transcriptase has been widely used in reverse transcription reactions of RNA to DNA. However, a reverse transcriptase has RNase H activity besides its RNA-dependent DNA polymerase activities and it is not stable at elevated temperature.

Chaperonins as thermal stabilizing factors. Chaperonins are a group of molecular chaperones and are a subset of the heat shock proteins (HSPs), whose members are widely distributed from prokaryotes to eukaryotes and first came to light because of their specific induction during the cellular response of all organisms to heat shock. It is now clear that the majorities of those proteins are expressed constitutively and abundantly in the absence of any stress, and genetic studies show that many of them are essential for cell viability under normal growth conditions (1,2,3). According to structure, molecular mass, and function, HSPs have previously been divided into several families (3); the stress-70 protein family, the stress-90 protein family, and the chaperonin family. In hyperthermophilic archaea which can grow above 80° C., chaperonin play an essential role in hindering protein denaturation (4,5,6). Many of the HSPs are or may be involved in de novo protein folding and assembling of proteins (2). One particular gene of interest for this invention is the gene encoding the Beta-subunit of a molecular chaperonin from the hyperthermophilic archaeon Pyrococcus (7), FIGS. 1,2.

Reverse Transcriptase—a multi functional polypeptide

The reverse transcriptase (RT) of the retrovirus Moloney murine leukemia virus (MMLV) is an essential enzyme involved in its life cycle and is commonly used as a reagent in modern molecular biology. Like other retroviral reverse transcriptases, the 76 kDa polypeptide from MMLV contains two separable activities: a DNA polymerase function encoded within its N-terminal portion and a ribonuclease H (RNAseH) function encoded in its C -terminus (FIGS. 3)(8–9). The combination of these two activities allows RT to convert single-stranded RNA into the double-stranded DNA needed for integration into the host chromosome. The RNaseH domain is responsible for the hydrolysis of the RNA portion of RNA-DNA hybrids, and this activity requires the presence of divalent cations (Mg2+ or Mn2+) that bind its active site (10). Today high resolution structures of the three members of this ubiquitous family have been determined by X-ray crystallography (11–14). The RT DNA polymerase activity is responsible for transcribing viral RNA into double-stranded DNA(15). RT is used extensively in recombinant DNA technology to synthesize cDNA from mRNA. One major problem with cDNA synthesis is to gain full-length cDNA from the RNA template, due to the tree dimension structure of mRNA molecules (16). One solution to this problem would be to increase the temperature during the cDNA synthesis to unfolded the different tree dimension structures of mRNA molecules. However since the RT DNA polymerase activity are decreasing relative fast at temperature above 65° C., due to thermal denaturation of the reverse transcriptase, this solution has not been possible so far. Another potential problem is the RNAseH activity of RT polypeptide. The mRNA poly(A)-oligo(dT) hybrid used as a primer for first-strand cDNA synthesis is degraded by RT RNAseH. Thus, at the outset of cDNA synthesis, a competition is established between RNaseH mediated deadenylation of mRNA and initiation of DNA synthesis, which reduces the yield of cDNA product (17). To removed the unwanted RNAseH activity the RT polypeptide from MMLV has been genetically changed either by entire removal of RNASEH C-terminal domain of the polypeptide or by point mutating essential amino acid, and thereby reducing the RNAseH activity (18).

BRIEF SUMMARY OF THE INVENTION

The present invention encompasses a surprising solution to the problems described above, by combining the stabilising effect of a thermostable Chaperonin with a reverse transcriptase.

BRIEF DESCRIPTION OF THE FIGURES

FIG. 2. This figure depicts the DNA sequence, which encodes the CpkB polypeptide used in this invention (SEQ ID NO: 1). Also shown is the corresponding amino acid sequence (SEQ ID NO: 2).

FIG. 5. This figure depicts the DNA sequence of RT2. Also shown is the corresponding amino acid sequence (SEQ ID NOs: 5 and 6).

Figure 1:
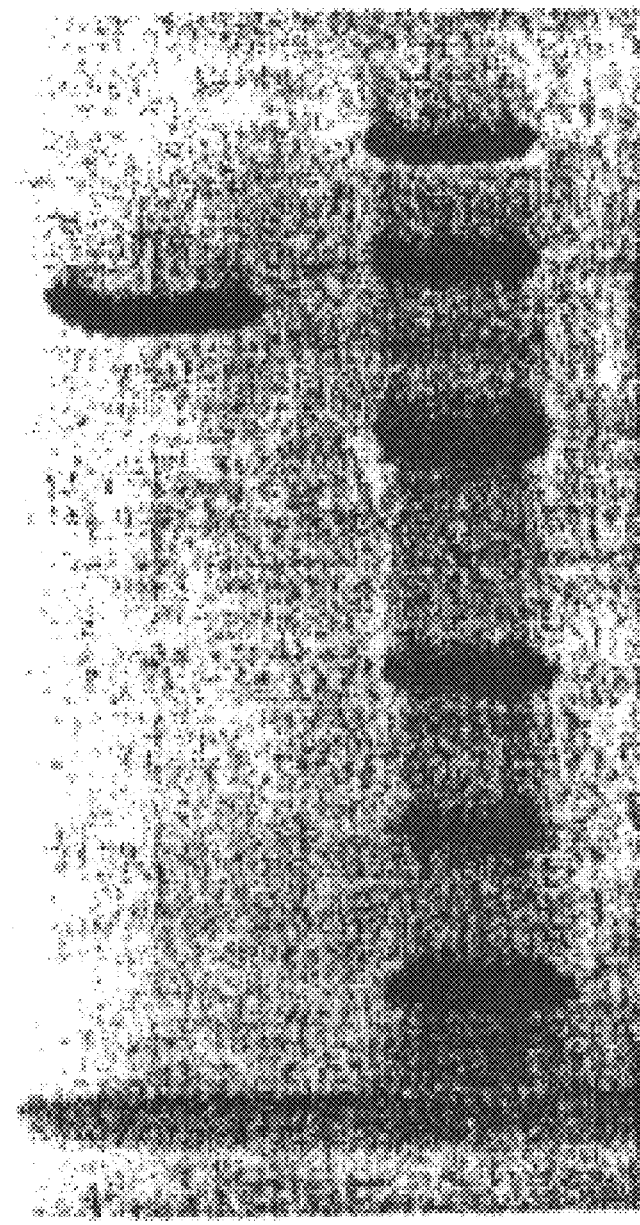
FIG. 1. This figure shows a SDS polyacrylamide gel loaded with the purified CpkB polypeptide and stained with Coomasie Blue. Lane 1 shows the purified CpkB protein used in this invention. The gene encoding CpkB is composed of 1641 nucleotides, encoding a polypeptide of 531 amino acids with a molecular mass of 57 kDa.

Lane 1: DNA marker
Lane 2: CpkB+RT1 enzyme mix 1:1
Lane 3: CpkB+RT1 enzyme mix 1:2
Lane 4: CpkB+RT2 enzyme mix 1:1
Lane 5: CpkB+RT2 enzyme mix 1:2
Lane 6: CpkB+RT1 enzyme mix 1:0.5
Lane 7: CpkB+RT2 enzyme mix 1:0.5
Lane 8: 100U RT1 alone
Lane 9: empty FIG. 8. RNAse activity at 4 different time points, 0.2 µg of 0.24–9.4 kb RNA ladder as template, 2.5 pmol biotinylated oligo(dT)20 and two different polypeptide mixes. After finish RT reaction time, the reactions were further incubated in 0, 15, 30, 60 minutes, before electrophorated on 1.0-% alkaline agarose gel and processed (developed).

Lane 1: Rtmix1: Time point 0 minutes
Lane 2: Rtmix1: Time point 15 minutes
Lane 3: Rtmix1: Time point 30 minutes
Lane 4: Rtmix1: Time point 60 minutes
Lane 5: Rt1: Time point 0 minutes
Lane 6: Rt1: Time point 15 minutes
Lane 7: Rt1: Time point 30 minutes
Lane 8: Rt1: Time point 60 minutes FIG. 9 Temperature reactivity using five different RT-PCR products amplified from the human 18S ribosomal RNA. M: Marker X174/HaeIII MIXES ARE Lane 1: 336 bp products (Rtmix1)
Lane 2: 603 bp products (Rtmix1)
Lane 3: 953 bp products (Rtmix1)
Lane 4: 1223 bp products (Rtmix1)
Lane 5: 1758 bp products (Rtmix1)
Lane 6: 336 bp products (RT1)
Lane 7: 603 bp products (RT1)
Lane 8: 953 bp products (RT1)
Lane 9: 1223 bp products (RT1)
Lane 10: 1758 bp products (RT1)

Figure 10:
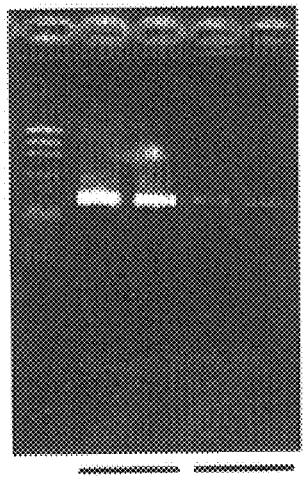

FIG. 10. Full-length Reverse transcription of DMD mRNA (14 KB). Human Duchnne muscular dystrophy (DMD) mRNA was reverse-transcribed using 3' specific primer and 0.1 µg human heart polyA+ RNA as template. 2 µl of the RT product were used as template in PCR reaction, which produced 379 bp amplicon at 5' end if the whole 14 KB cDNA have been synthesized. MIXES ARE Lane 1: Rtmix1
Lane 2: Rtmix2
Lane 3: RT1 polypeptide
Lane 4: RT2 polypeptide.

DETAILED DESCRIPTION OF THE INVENTION

Figure 2:
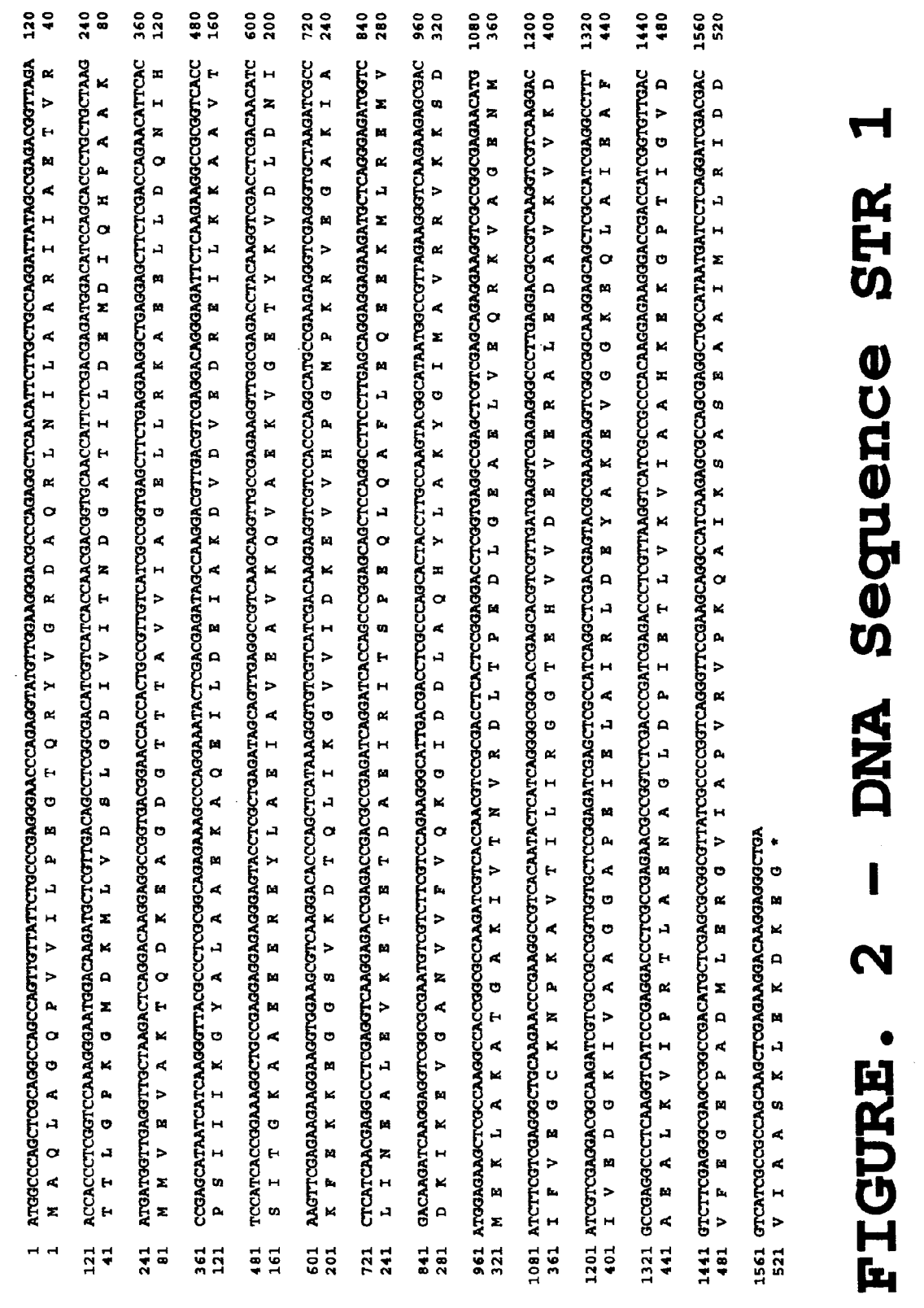

One particular gene of interest for this invention is the gene encoding the β-subunit of a molecular Chaperonin from the hyperthermophilic archaeon Pyrococcus (7), (FIGS. 1,2). The cpkB gene is composed of 1,641 nucleotides encoding a protein (546 amino acids) with a molecular mass of 59,140 Da. The enhancing effect of CpkB on enzyme stability had been examined in the combination of CpkB and yeast alcohol dehydrogenase (ADH) (21), but no relation with the functioning of reverse transcriptase had been proposed or established prior to the present invention.

The present invention is related to the discovery that the CpkB polypeptide together with a reverse transcriptase generates a system having improved DNA polymerase activity at relative high temperatures compared to a reverse transcriptase alone. The purified CpkB polypeptide of the present invention together with a reverse transcriptase can therefor be used to effectively synthesise cDNA from mRNA at relative high temperature.

The invention is further related to the discovery that the CpkB polypeptide inhibits the RNase H activity normally associated with the MMLV wild type reverse transcriptase. It possibly binds within a small part of the RNase H domain of the MMLV reverse transcriptase and thereby blocks its RNase H activity statically or enzymatically.

The present invention describes a method for improved reverse transcription at high temperatures, wherein the reverse transcriptase exhibits enhanced thermal stability and substantially reduced RNase H activity. A method is revealed for reverse transcribing RNA into DNA, wherein the reverse transcription reaction is performed at temperatures at least above about 42° C. and wherein the reverse transcriptase employed herein exhibits enhanced thermal stability and substantially reduced RNase H activity.

In a preferred embodiment, the present invention relates to a method for enhancing thermal stability and substantially reducing RNase H activity of a reverse transcriptase in a reverse transcription reaction of RNA to DNA, wherein the thermostability and substantially reduced RNase H activity is obtained by adding one or more agents having thermostabilising activity on and inhibiting RNase H activity of the reverse transcriptase. A method for preparing cDNA from mRNA is described, comprising contacting mRNA with a reverse transcriptase having RNA-dependent DNA polymerase activity and exhibiting enhanced thermostability and substantially reduced RNAse H activity, and subsequently isolating said cDNA. In that preferred embodiment, said enhanced thermostability and substantially reduced RNase H activity is induced by adding one or more stabilising agents to said preparation. Said reverse preparation can easily yield a full-length cDNA.

An even more preferred embodiment relates to a method for conducting a reverse transcription reaction, wherein a stabilising agent is combined with a polypeptide that exhibits reverse transcriptase activity, wherein said stabilising agent prevents thermal denaturation, inhibits RNase H activity and/or enhances thermostability of said polypeptide.

The reverse transcription described in the present invention are carried out at any temperature in the range from about 42° C. to about 95° C., such as at 41.5° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C. or 95.5° C. and preferably at a temperature at least above 42° C. and most preferably still, at a temperature at least above 65° C.

The method for improved reverse transcription described in the present invention is stabilised by the addition of an agent that can be an enzyme. Said stabilising agent can more specifically be selected from the group consisting of members of the heat shock proteins, and in a preferred embodiment of the invention, the stabilising agent is a β-subunit of a Chaperonin which can be derived from Hyperthermoplilic Archaeon Pyrococcus sp. or alternatively be derived synthetically.

The present invention relates to a gene (cpkB) which encodes a polypeptide preventing thermal denaturation and enhancing thermostability of a reverse transcriptase. The nucleic acid sequence of said gene is shown in SEQ ID NO: 1. Furthermore, said polypeptide inhibits the RNAse H activity associated with the reverse transcriptase by binding to the RNase H domain of said reverse transcriptase. The invention thus also relates to the polypeptide CpkB comprising an amino acid sequence as shown in sequence STR1, FIG. 2 and SEQ ID NO: 2, or to degenerated variants thereof.

Figure 4:
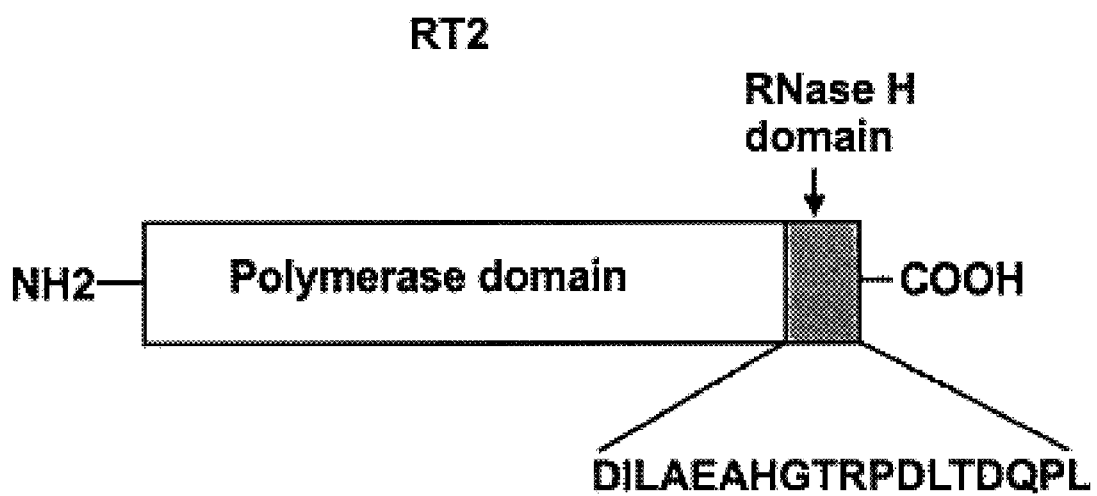
FIG. 4. RT2 represents a C-terminal truncated version of RT1, which is composed of 515 amino acids with a molecular mass of 57.6 kDa, having an intact polymerase domain and a part of the RNase H domain (SEQ ID NO: 4).
Figure 6:
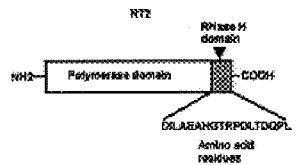
FIG. 6. This figure shows a schematic representation of CpkB, RT1, RT2, and a mixture of CpkB+RT1 and CpkB+RT2 and the enzymatic activities and predicted structure of the polypeptides FIG. 7. Temperature reactivity, this figure depicts a 1% agarose gel showing a RT-PCR set up. After reverse transcription a specific part of the Glyceraldehyde 3-Phosphate Dehyderogenase gene were amplified by PCR, following enzyme was used for the RT reaction.

The invention also relates to a gene encoding a reverse transcriptase as shown in SEQ ID NO: 5, comprising the amino acid sequence shown in sequence STR2, FIGS. 4,5 and SEQ ID NO:6 or degenerate variants thereof.

In the method for improved reverse transcription that is described in the present invention, a reverse transcriptase is embodied as encoded by said gene shown in SEQ ID NO: 5. The reverse transcriptase is preferably selected from the group consisting of reverse transcriptase from AMV (Avian Myeloblastosis Virus), M-MuLV (murine M-MuLV pol gene) and HIV-1 (HIV virus) and degenerated or truncated or mutated versions thereof. In a most preferred embodiment again, said reverse transcriptase is derived from Moloney murine leukemia virus.

The stabilising agent of the present invention prevents thermal denaturation and/or enhances conformational reformation of the reverse transcriptase used in the reaction and significantly reduces its RNase H activity to substantially no RNase H activity.

The present invention also relates to a vector containing any of the above described genes of the invention, and to any hosts transformed, with a vector of the invention. A clone expressing cpkB, herein called DSB-KOD1, is a most preferred embodiment of the invention.

A preferred embodiment of the invention is a combination of two fusion proteins comprising
  a) A polypeptide having RNA-dependent DNA polymerase activity, and
  b) A polypeptide being able to prevent thermal denaturation and to enhance thermostability of said polypeptide of step a).

Another preferred embodiment of the invention relates to a combination of two fusion proteins comprising
  a) A polypeptide having RNA-dependent DNA polymerase activity, and
  b) A polypeptide being able to prevent thermal denaturation and to enhance thermostability of said polypeptide of step a), wherein the polypeptide of step a) at the same time has reduced RNase H activity compared to a reverse transcriptase alone.

Another even more preferred embodiment of the invention relates to a combination of two fusion proteins comprising a protein complex system having RNA-dependent DNA polymerase activity at relative high temperatures, and reduced RNase H activity.

Another aspect of the invention relates to a method for producing the polypeptide CpkB, comprising culturing transformed hosts of the invention under conditions under which they express the polypeptide which has a thermal stabilisation effect on said reverse transcriptase. In yet another aspect of the invention, a polypeptide-complex of a stabilising agent with a polypeptide that exhibits reverse transcriptase activity is produced, wherein said stabilising agent prevents thermal denaturation, inhibits RNase H activity and/or enhances thermostability of said polypeptide.

The invention furthermore relates to a method for preparing a DNA molecule, said method comprising
  a) Mixing an mRNA template with a reverse transcriptase and the CpkB polypeptide or with said polypeptide-complex, thereby stabilising said DNA polymerase activity at a relative high temperature and substantially reducing RNase H activity, and
  b) Incubating said mixture under conditions sufficient to make a first DNA molecule complementary to said mRNA template, which can be a full-length cDNA or a partial cDNA. This method can comprise a 2-step reaction, wherein the stabilising agent and the polypeptide are added separately in each step, or wherein the stabilising agent and the polypeptide are added simultaneously and are present in both steps.

The nucleic acids in the reaction may be purified or unpurified.

As known by a person skilled in the art, the choice of primers to initialise a PCR reaction is individual and has to be adjusted for each reaction anew. As a general rule, but not intended to limit the present invention, said one or more cDNA primer do not include a poly or oligo dT tail in the 5'-end. Furthermore, said one or more cDNA primer should have the following structure 5'-NxTTA-3' or 5'NxCTA-3' or 5'-NxTCA-3', wherein N is A, G, T, or C, and x is an integer $1 \leq x \leq 20$.

In a specific embodiment, the primers of the invention are used in in situ amplification reactions, performed on samples of fresh or preserved tissues or cells. In in situ reactions, it is advantageous to use methods that allow for the accurate and sensitive detection of the target directly after the amplification step.

Any PCR reaction might be employed not only to translate an RNA template into DNA, but also to amplify the so obtained DNA. The present invention therefore also enscopes a method comprising incubating said first DNA molecule under conditions sufficient to transcribe a second DNA molecule complementary to said first DNA molecule, wherein said first and second DNA molecules can form a double stranded DNA molecule. Furthermore, said double stranded DNA molecule can of course be a full-length cDNA.

The invention also relates to a kit for the preparation of cDNA from mRNA comprising a carrier being compartmentalised to receive in close confinement therein one or more containers, wherein
  (a) First container contains the CpkB polypeptides and a reverse transcriptase polypeptide,
  (b) A second container contains the CpkB polypeptide alone,
  (c) A third container contains a buffer and the nucleoside triphosphates, and
  (d) A fourth container contains oligo (dT) primer, wherein said reverse transcriptase polypeptide may be used for the preparation of a full-length cDNA.

In one embodiment of the invention, said kit for the preparation of cDNA, comprises a container containing a stabilised agent and a polypeptide with reverse transcriptase activity, or a polypeptide-complex as described above.

In another embodiment, said kit further comprises one or more additional containers selected from the group consisting of:

(a) a container containing one or more nucleoside triphosphates, (b) a container containing an oligo (dT) primer, and (c) a container containing a buffer suitable for use in transcribing a cDNA.

A preferred embodiment of the invention further relates to a composition for reverse transcription of a target ribonucleic acid (RNA) comprising a single lyophilizate comprising:

a) an effective amount of a reverse transcriptase;

b) one or more stabilising agents having thermostabilising and RNase H inhibiting activity selected from the group consisting of chaperones and heat shock proteins;

c) deoxyribonucleotide triphosphates and ribonucleotide triphosphates, wherein when said lyophilizate is reconstituted by addition of an aqueous solvent, the resulting solution will amplify a single-stranded RNA molecule having a target nucleotide sequence region when contacted with one or more suitable oligonucleotide primers under appropriate nucleic acid amplification conditions.

DETAILED DESCRIPTION OF THE PREFERRED EMBODIMENTS

The present invention relates to a method for preventing thermal denaturation and enhancing of the thermostability of a reverse transcriptase for use in recombinant DNA techniques.

This stabilising effect is best achieved under cyclic temperature profiles used as standard procedures in many PCR reactions. In the present invention, thermal denaturation of the reverse transcriptase is not fully inhibited, but instead, the ability of the enzyme to regain its native configuration at a lowered temperature is helped and promoted by adding the stabilising agent to said reaction.

The invention also relates to a method for reducing RNase H activity, which degrades mRNA template during first-strand synthesis, by interacting a Chaperonin with a reverse transcriptase, and thereby inhibiting the RNase H activity of said reverse transcriptase. The RNase H activity is substantially inhibited meaning at least about 200% inhibition compared to wild type RNase H activity. In an especially preferred embodiment of this invention, the RNase H activity is in fact reduced to substantially no RNase H activity.

Figure 8:
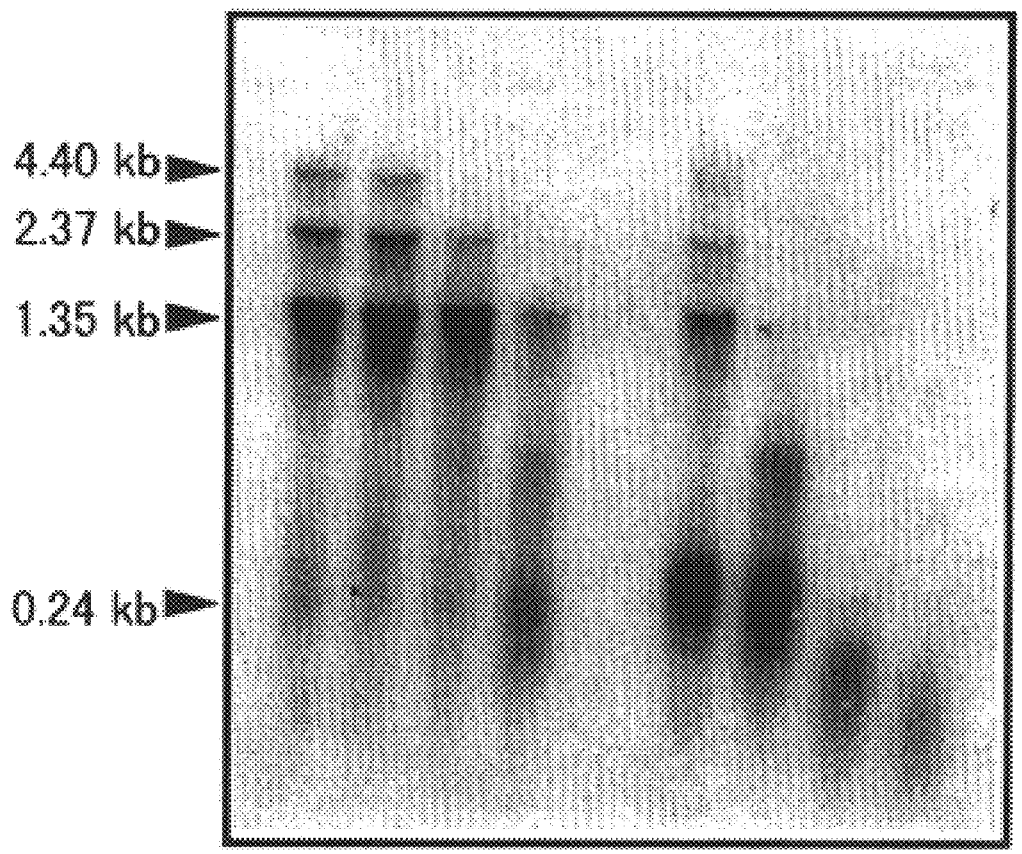

By the term "inhibiting RNase H activity", the function of a mixture of CpkB and reverse transcriptase is intended, that inhibits an RNase H activity and that allows the preparation of cDNA without significant degradation of the mRNA template during first-strand synthesis (FIG. 8).

Recombinant plasmids constructed as described therein, carry nucleic acid sequences encoding for polypeptides such as both a Chaperonin and a reverse transcriptase for use in recombinant DNA technology to synthesize cDNA from mRNA without the problem of getting truncated cDNA molecules, often associated with reverse transcriptases that preferably function at low temperature.

By the term "relative low temperature" a temperature below 65° C. is intended.

The temperatures used for the reverse transcription reactions described in the present invention are changing in a cyclic behaviour. As known by the person skilled in PCR techniques, a PCR reaction will make use of different temperature settings to achieve the translation and amplification of a given template RNA by a reverse transcriptase. In the present invention, the temperatures used are in one embodiment optimised to 10 minutes at about 42° C. followed by 2 minutes at about 60° C. and 8 minutes at about 50° C. The given temperatures are mean temperatures of intervals: 50° C. relating to an interval of 60–95° C. and 50° C. relating to an interval of 40–65° C. The temperature profiles are incorporated into a temperature cycle and said cycle is run between 8–20 times. These parameters are meant as examples for an optimised cycling PCR profile, but are in no way meant to be limiting. In general, the present invention makes it possible to make use of higher PCR temperatures compared to those used in PCR reactions wherein no stabilising agent is used.

By the term "degenerate variants", cloned genes are intended, having variations of DNA sequence, which still encode the same amino acid sequence.

A preferred embodiment of the present invention is a polypeptide shown in RT2, that comprises a portion of an RT gene derived from M-MLV which encodes a DNA polymerase and a part of the RNase H domain. This preferred embodiment interacts with the CpkB polypeptide in a domain localised to the first amino acids of the RNase H domain and/or in the polymerase domain (FIG. 4).

The protein named RT2 has both DNA polymerase activity and RNase H activity.

When RT2 and CpkB are combined, a polypeptide mixture is obtained that prevents thermal denaturation and enhances thermostability of said (RT2) polypeptide, which is a reverse transcriptase.

Any transformed host of the invention may be cultured under protein producing conditions according to any of the methods, which are known to those skilled in the art.

A polypeptide mixture consisting of CpkB and a reverse transcriptase produced by a method according to the present invention, may be used to prepare cDNA from RNA by, for example, by hybridising an oligo (dT) primer or any other complementary primer to the mRNA. The synthesis of a complete cDNA may be accomplished by adding the polypeptide mixture and all four deoxynucleoside triphosphates. Using the polypeptide mixture as described in the present invention, allows for the preparation of full-length cDNA from mRNA at high temperature without denaturation of said reverse transcriptase.

Furthermore, using the polypeptide mixture described in the present invention allows for the preparation of full-length cDNA from mRNA at a high temperature and with a reduced RNase H activity of the reverse transcriptase, due to the interaction of the CpkB with the reverse transcriptase.

The resulting RNA-DNA hybrid may, for example, be tested with alkali or RNase H to selectively hydrolyse the RNA to leave the cDNA, which may successively be converted to a double-stranded form in a second DNA reaction, catalysed by a reverse transcriptase or any other DNA polymerase.

The polypeptide mixture described in the invention is ideally suited for incorporation into a kit for the preparation of cDNA from RNA. Such a kit may comprise a carrier means being compartmentalised to receive a closed confinement therein, one or more container means, such as vials, tubes, and the like, each of said container means comprising one of the separate elements of the method used to prepare cDNA from RNA.

The following examples are illustrative but not limiting of the methods and compositions of the present invention. Any suitable modifications and adaptations, which are obvious to one of ordinary skill in the art of recombinant DNA techniques, are within the spirit and scope of the present invention.

EXAMPLES

Example 1

The DNA fragment carrying the cpkB gene was amplified by PCR using two primers which have a NcoI and a BamHI recognition sequence 5'-GGCAGGGGCCATGGCCCAGCTCGCAGGCCAGC-3'(SEQ ID NO: 7) AND 5'-GCGCAAAAGGGATCCAAGGTCATCAGTCAAGG-3'(SEQ ID NO: 8) DNA from Archaeon Pyrococcus was used as template.

The amplified DNA was cloned between NcoI and BamHI sites of pET-c plasmid (Novagen), and the constructed plasmid was designated pCpkB. The pCpkB construct was DNA sequenced from both directions in the plasmid to check for the correct sequence of the pCpkB constructs. pCpkB was overproduced in E. coli DH5α (19), and purification was carried out.

E. coli harboring pCpkB were induced by 0.1 mM IPTG at mid-exponential phase and incubated for 8 hours at 37° C. The cells were centrifugated and the pellet was washed with 100 mM phosphate buffer (pH 8.0). The cells were disrupted by adding 0.1% SDS/Triton×100 and the supernatant was recovered by centrifugation at 10,000×g for 30 minutes at 4° C. The supernatant was heat treated for 85° C. for 30 minutes and centrifuged again at 20,000×g for 20 minutes at 4° C. The supernatant was filtered through a 0.45 μM filter and the filtrate was applied to an anion -exchange column (HiTrap Q; Amersham Pharmacia). First the HiTrap column was equilibrated on 50 mM phosphate buffer (pH 8.0), and the pCpkB filtrate was eluted with a linear gradient of NaCl by using a fast protein liquid chromotography system (Pharmacia). As shown (FIG. 1) the Chaperonin CpkB was purified and expressed in E. coli from a genetic construct as described above.

Example 2

To illustrate the CpkB's effect of preventing thermal denaturation of RT1 and RT2 at 65° C., 105 copies of the G3PDH (Glyceraldehyde 3-Phosphate Dehydrogenase) in vitro transcript were reverse transcribed.

Figure 3:
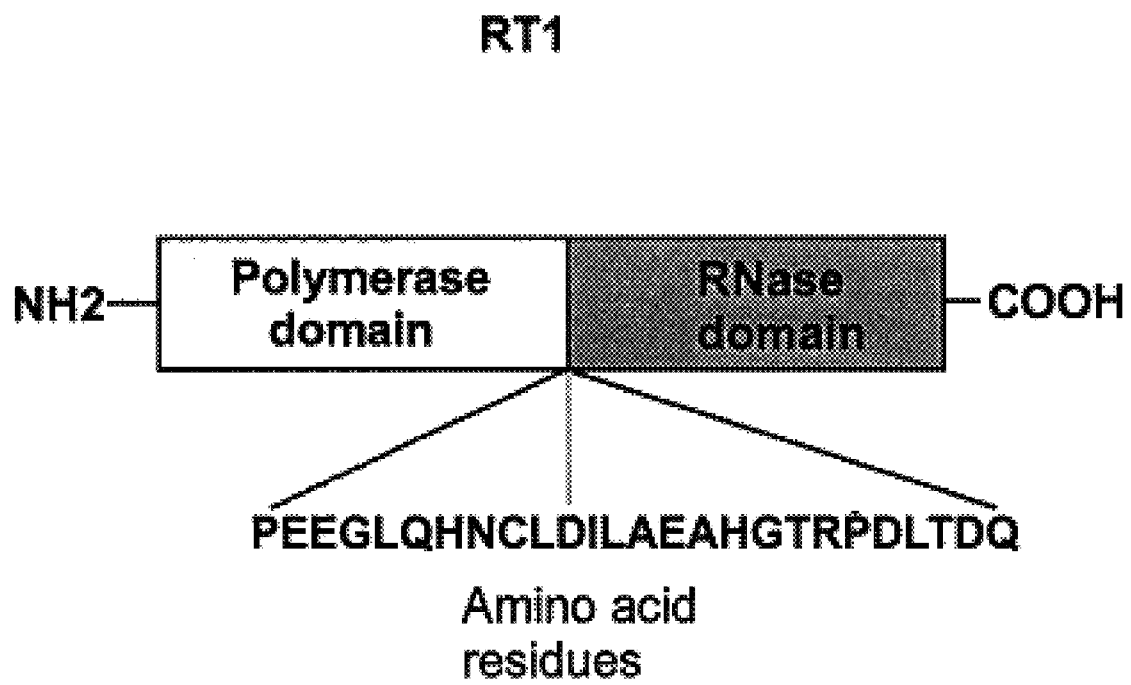
FIG. 3. RT1 represents the full length RT from M-MLV, which is composed of two domains. The N-terminal domain having polymerase activity and the C-terminal domain having RNase H activity. The sequence at the junction between the two domains is indicated (SEQ ID NO: 3) according to (10 ).

The reverse transcript RT1 and RT2 as shown in FIGS. 3, 4, 5 was constructed from a plasmid pMov-3 containing the MmuLV pol gene (20). Standard PCR techniques were used for construction of RT1 and RT2 genes. The amplified DNA was cloned between NcoI and BamHI sites of plasmid pET-c (Novagen), and the constructed plasmid was designated pRT1 and pRT2. Both constructs were DNA sequenced from both directions in the plasmid to check for the correct sequence of said constructs. The reverse transcriptase was overproduced in E. coli DH5α (19), and purification was carried out. E. coli cells harboring pRT1 and pRT2 were induced by 0.1 mM IPTG at mid-exponential phase and incubated for 8 hours at 37° C. The cells were centrifuged and the pellet was washed with 100 mM phosphate buffer (pH 8.0). The rest of the purification procedure was carried by modified a purification method described according to ref 9 and 21.

Standard condition for cDNA Synthesis
Rtmix1: CpkB+RT1 enzyme mix 1:1 (100U RT1+CpkB)
Rtmix2: CpkB+RT2 enzyme mix 1:1 (100U RT1+CpkB)

The following components were combined: 4.0 μl RT 5X Buffer (250 mM Tris-HCl, pH 8.3, 375 mM KCl, 15 mM MgCl2, 50 mM DTT); 2.0 μl 5 mM dNTP; 2.0 μl T20V Primer(10 μM); 2.0 μl total RNA (0.25–1.0 μg); 9.0 μl RNase-free H2O; 1.0 μl Rtmixx (X=1 or 2). Incubated at 42° C. for 10 minutes and the temperature increased to 65° C. and incubate for 40 minutes more.

PCR setup: 1–2 μl of the reverse transcriptase reaction is used as template in a standard 50 μl PCR reaction, a total of 30–35 cycles will be sufficient for most applications. High quality, intact RNA is essential for successful full-length cDNA synthesis. RNA should be devoid of any RNase contamination and aseptic synthesis. RNA should be devoid of any RNase contamination and aseptic conditions should be maintained. The cDNA synthesis should be performed using thin-walled PCR tubes in a thermocycler with heatable lid to avoid evaporation (alternatively, overlay with oil). Oligo(dT)20 is recommended for the priming of polyadenylated RNA, and allows the detection of multiple transcripts from a single first-strand reaction. Random hexamers (20–40 pmol/reaction) are efficient primers for the detection of multiple RT-PCR targets, and particularly useful in prokaryotic systems. If random hexamers are used, the first-strand synthesis must be incubated for 10 min at 25° C. followed by 30 min at 65° C. to extend the primers prior to increasing the reaction temperature for final extension. Gene-specific primers should be used at 10–20 pmol/reaction (0.5–1.0 μM). The unit definition of the purified RT1 and RT2 reverse transcriptase. One unit of DNA polymerase activity is the amount of enzyme which incorporates 1 nmol of dTTP into acid insoluble form in 10 minutes at 37° C. in 50 mM Tris-HCl, pH 8.3, 40 mM KCl, 10 mM DTT, 7 mM MgCl2, 0.1 mg/ml BSA, 0.5 radiolabeled dTTP and 130 μg/ml rA400:dT50

Example 3

Figure 7:
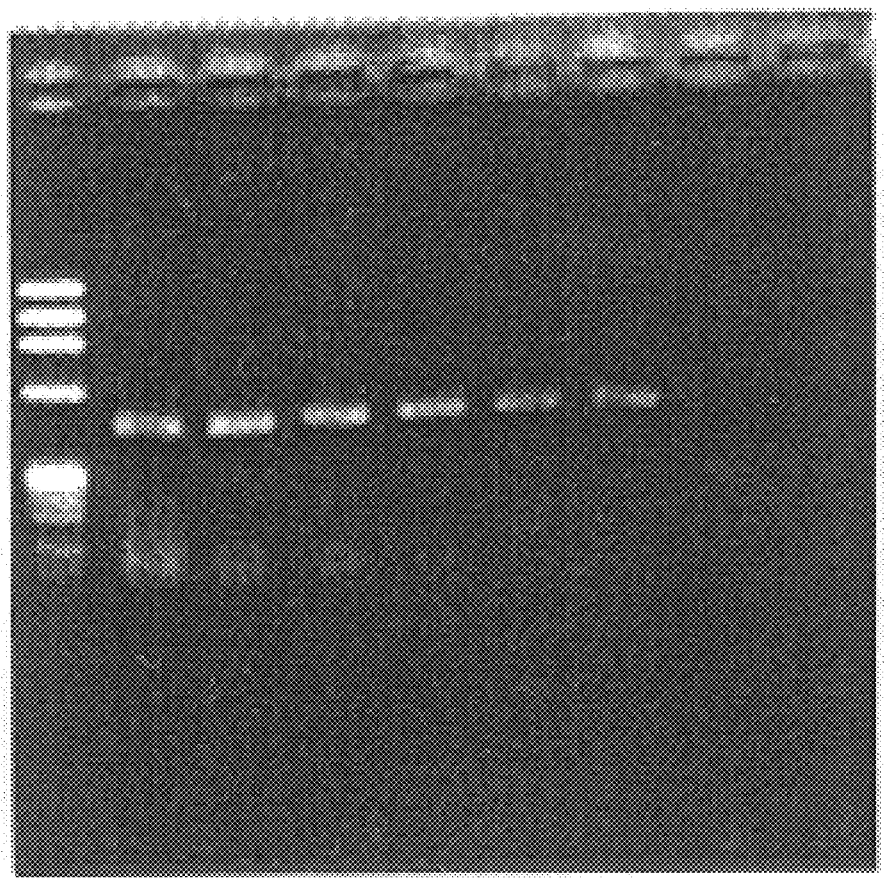

The Temperature reactivity experiment (FIG. 7) was performed using standard condition for cDNA Synthesis. Different combinations of polypeptide CpkB, RT1 or RT2 were tested. Optimal results, shown in FIG. 7, lanes 1–2, were obtained using 100 Units of either RT1 or RT2 in combination with 10 pg CpkB.

Example 4

The RNase H activity experiment (FIG. 8) was performed using standard condition for cDNA Synthesis. The temperature reactivity using five-target (FIG. 9) gene fragment, was performed using standard condition for cDNA Synthesis. To investigate if the Rtmix1 had reduced RNase H activity compare to RT1 the integrity of a 0.24–9.4 kb RNA ladder was investigated. A biotinylated oligo(dT)20 was used for detection. After conversion to DNA-RNA hybrid form during reverse transcriptase catalyzed DNA synthesis, samples was taken our at four different time intervals (0, 15 60 90 minutes). FIG. 8 shows that with Rt1 alone the full-length RNA ladder template was degraded totally after 15 min of synthesis. In contrast, with Rtmix1 the RNA was intact even after 60 minute. Identical results were obtained with the Rmix2 result not shown. This experiment (FIG. 8) indicate that the Rtmix1–2 has an inhibitory effect on the RNase H activity of the reverse transcriptase. The same experiment was performed using the Rtmix2 with similar results, data not shown.

Example 5

Human 18S ribosomal RNA was reverse transcribed to test whether RNA template forming a high degree of secondary structure could be reverse transcribed using the Rtmix2. A 3' specific antisence primer and 100 pg HeLa total RNA as template (FIG. 9). The experiment was performed as described in materials and methods. As shown (FIG. 9) the Rtmix2 was able to reverse transcribed all the five different target sized within the 18S ribosomal RNA, where the RT2 alone did not succeed in reverse transcribed particular the larger gene fragments (FIG. 9).

Example 6

The Full-length RT experiment (FIG. 10)using the DMD mRNA as target was performed using standard condition for cDNA Synthesis. When measuring the ability of Rmix2 to synthesize a cDNA copy of long RNA (obtain full-length cDNA) human Duchne muscular dystrophy (DMD) mRNA (14 kb) was reverse transcribed using 3' specific antisense primer and 0.1 µg human heart polyA+ RNA as template as described in materials and methods. 2 µl of the RT product were used as template in PCR reaction, which produced a 379 amplicon at the 5' end of the 14 kb cDNA. As shown (FIG. 10)the Rtmix2 was able to reverse transcribed through all 14 kb, whereas the RT2 polypeptide alone did only give a very faint band on the agarose gel after 25 cycle of PCR.

Recently evident shows an 18 residue N-terminal extension outside the region homologous to *E. coli* RNase HI is important for structural stability of the RNase H domain of the MMLV RT (10). Therefore, this region should be considered part of the RNase H domain (10). In this intention those 18 residue have been included in the RT2 construct which together with the CpkB prevent the reverse transcriptase from thermal denaturation.

LIST OF REFERENCES:

1. Ellis, R. J. Molecular chaperones: the plant connection. Science 250:954–59 (1990).
2. Ellis, R. J. Molecular chaperones. Annu. Rev. Biochem. 60:321–347 (1991).
3. Gething, M. J. et al., Protein folding in the cell. Nature 355: 33–35 (1992).
4. Imanaka, T. et al., Gene 164:153–156 (1995).
5. Kagawa, H. K. et al., J. Mol Biol. 253: 712–725.
6. Quaite-Randall, Q. et al., J. Biol. Chem. 270: 28818–28823.
7. Imanaka, T. et al., Applied and Environmental Microbiology 63:785–789 (1997).
8. Tanese, N., et al Domain structure of the Moleney murine leukemia virus reverse transcriptase: Mutational analysis and separate expression of the DNA polymerase and RNase H activities. PNAS 85: 1777–1781, (1998).
9. Gerard, G. F. and Grandgenett, D. P., "Purification and Characterization of the DNA Polymerase and RNase H Activities in Moloney Murine Sarcoma-Leukemia Virus," J. Virology 15(4): 785–797 (1975).
10. Marqusee, S. et al., "Folding the Ribonuclease H Domain of Moleney Murine Leukemia Virus Reverse Transcriptase Requires Metal Binding or short N-Terminal Extension" PROTEINS 33:135–143 (1998).
11. Yang. W. et at., Science 249:1398–1405 (1990).
12. Katayanagi, K., Nature 347:306–309 (1990).
13. Ishikawa, k., J. Mol. Biol 230:529–542.
14. Davies, J. D., Science 252:88–95.
15. Varmus, H. (1982), in Weiss, R., et al. (eds.), RNA Tumor Viruses, Cold Spring Harbor Laboratory, pp. 410–423.
16. Berger, S. L., et al., Biochem. 22:2365–2373 (1983).
17. U.S. Pat. No. : 5,668,005; 5,405,766 and 5,244,797.
18. Maniatis, T. In:Molecular Cloning, A Laboratory Manual, Cold Spring Harbor Laboratory Press, pp. 213 and 231 (1982).
19. Harbers, K. et al., PNAS 78, 7609–7613 (1981).
20. Golomb, M. et al., J. Virological Methods, 1:157–165 (1980).
21. Goedken, E. R., Marqusee, S., PROTEINS: Structure, Function, and Genetics 33; 135–143 (1998).

What is claimed is:

1. A method for reverse transcribing RNA into DNA comprising contacting the RNA with a reverse transcriptase, and a chaperone protein, at a temperature above 42° C., whereby the reverse transcriptase has enhanced thermostability and substantially reduced RNase H activity.

2. In a method for reverse transcribing RNA into DNA comprising contacting the RNA with a reverse transcriptase, wherein the improvement comprises performing said contacting in the presence of a chaperone protein, whereby the reverse transcriptase has enhanced thermostability and substantially reduced RNase H activity.

3. A method for enhancing thermal stability and substantially reducing RNase H activity of a reverse transcriptase comprising employing said reverse transcriptase, in a reverse transcription reaction of RNA to DNA, in the presence of a chaperone protein.

4. A method for reverse transcribing RNA into DNA comprising contacting the RNA with a reverse transcriptase, and a chaperone protein at a temperature above 42° C., whereby the reverse transcriptase has substantially reduced RNase H activity.

5. In a method for reverse transcribing RNA into DNA comprising contacting the RNA with a reverse transcriptase, wherein the improvement comprises performing said contacting in the presence of a chaperone protein, whereby the reverse transcriptase has substantially reduced RNase H activity.

6. A method for substantially reducing RNase H activity of a reverse transcriptase comprising employing said reverse transcriptase, in a reverse transcription reaction of RNA to DNA, in the presence of a chaperone protein.

7. A method for preparing DNA from RNA comprising contacting the RNA with a reverse transcriptase, wherein the contacting is in the presence of a chaperone protein, whereby the reverse transcriptase has substantially reduced RNase H activity and enhanced thermostability.

8. A method for preparing DNA from RNA comprising contacting the RNA with a reverse transcriptase, wherein the contacting is in the presence of a chaperone protein, whereby the reverse transcriptase has substantially reduced RNase H activity.

9. A method for reverse transcribing RNA to DNA comprising contacting the RNA with a reverse transcriptase, and a chaperone protein, whereby the reverse transcriptase has enhanced thermostability and substantially reduced RNase H activity.

10. A method for reverse transcribing RNA into DNA comprising contacting the RNA with a reverse transcriptase, and a chaperone protein, whereby the reverse transcriptase has substantially reduced RNase H activity.

11. A method of any one of claims 2–3 or 5–10 wherein the method is performed at a temperature above 42° C.

12. A method of claim 11 wherein he method is performed at a temperature above 65° C.

13. A method according to any one of claim 1–10 wherein the DNA is cDNA.

14. A method according to any one of claims 1–10 wherein the RNA is mRNA.

15. A method according to any one of claims 1–10 wherein the DNA is full length cDNA.

16. A method according to any one of claims 1–10 wherein the RNA is mRNA and the DNA is cDNA.

17. A method according to any one of claims 1–10 additionally comprising isolating the DNA.

18. A method according to any one of claims 1–10 wherein the RNA is mRNA, and the DNA is cDNA and the method additionally comprises isolating the cDNA.

19. A method according to any one of claims 1–10 wherein the chaperone protein is CpkB.

20. A method according to any one of claims 1–10 wherein the chaperone protein is a Beta subunit of a chaperonin.

21. A method according to any one of claims 1–10 wherein the chaperone protein is from Hyperthermophilic Archaeon Pyrococcus sp.

22. A method according to any of claims 1–10, wherein the reverse transcriptase is selected from the group consisting of reverse transcriptases from AMV (Avian Myeloblastosis Virus), M-MuLV (murine M-MuLV pol gene), HIV-1 (HIV virus), and degenerated or truncated or mutated versions thereof.

23. A method according to claim 22, wherein the reverse transcriptase is derived from Moloney murine leukemia virus.

24. A method according to any one of claims 1–10 wherein the RNase H activity is reduced to substantially no RNase H activity.

25. A method according to any one of claims 1–10 comprising separately adding the reverse transcriptase and the chaperone protein to the RNA.

26. A method according to any one of claims 1–10 comprising adding a mixture of the reverse transcriptase and the chaperone protein to the RNA, or simultaneously adding the reverse transcriptase and the chaperone protein to the RNA.

27. A method for preparing a DNA molecule, said method comprising
   a) mixing an mRNA template with one or more cDNA primers to form a first mixture,
   b) adding to the first mixture a chaperone protein and a reverse transcriptase, separately, or simultaneously, or adding to the first mixture a chaperone protein-reverse transcriptase; combination or mixture, to thereby form a second mixture and substantially reduce any RNase H activity of the reverse transcriptase,
   c) incubating said second mixture under conditions sufficient to transcribe a first DNA molecule complementary to said mRNA template.

28. A method according to claim 27, wherein said one or more cDNA primer does not include a poly or oligo dT tail in the 5' end.

29. A method according to claim 28, wherein said one or more cDNA primer has the following structure 5'-$N_x$TTA-3' or 5'-$N_x$CTA-3' or 5'-$N_x$TCA-3, wherein N is A, G, T, or C, and x is an integer $1 \leq x \leq 20$.

30. A method according to any one of claims 27–29, wherein said first DNA molecule is a full length cDNA.

31. A method according to any one of claims 27–29, further comprising incubating said first DNA molecule under conditions sufficient to transcribe a second DNA molecule complementary to said first DNA molecule.

32. A method according to claim 31, wherein said first DNA molecule is a full length cDNA.

33. A method according to claim 31, wherein said first and second DNA molecules form a double stranded DNA molecule.

34. A method according to claim 33, wherein said first DNA molecule is a full length cDNA.

35. A method according to claim 33, wherein said double stranded DNA molecule is a full-length cDNA.

36. A composition comprising CpkB and a reverse transcriptase.

37. A kit for the preparation of cDNA comprising a first container containing CpkB and a second container containing a reverse transcriptase; or a container containing CpkB and a reverse transcriptase mixture.

38. A kit according to claim 37, further comprising one or more additional containers selected from the group consisting of:

(a) a container containing one or more nucleoside triphosphates, (b) a container containing an oligo (dT) primer, and (c) a container containing a buffer suitable for use in transcribing a cDNA.

39. A composition for reverse transcription of a target ribonucleic acid (RNA) comprising a single lyophilizate comprising:

a) an effective amount of a reverse transcriptase;

b) CpkB;

c) deoxyribonucleotide triphosphates and ribonucleotide triphosphates, wherein when said lyophilizate is reconstituted by addition of an aqueous solvent, and the resulting solution will amplify a single-stranded RNA molecule having a target nucleotide sequence region when contacted with one or more suitable oligonucleotide primers under appropriate nucleic acid amplification conditions.

* * * * *

UNITED STATES PATENT AND TRADEMARK OFFICE
CERTIFICATE OF CORRECTION

PATENT NO. : 6,271,004 B1
DATED : August 7, 2001
INVENTOR(S) : Warthoe

It is certified that error appears in the above-identified patent and that said Letters Patent is hereby corrected as shown below:

Column 25,
Line 37, after transcribing RNA delete "to", and insert -- into --.
Line 48, delete "he method", and insert -- the method --.

Column 26,
Line 31, delete "transcriptase;", and insert -- transcriptase --.

Signed and Sealed this

Thirtieth Day of April, 2002

Attest:

JAMES E. ROGAN
Attesting Officer          Director of the United States Patent and Trademark Office